US005343858A

United States Patent [19]

Winefordner et al.

[11] Patent Number: 5,343,858
[45] Date of Patent: Sep. 6, 1994

[54] SECOND STAGE DEMAND BREATHING REGULATOR

[75] Inventors: Carl Winefordner, El Toro; Frank Hermansen, Newport Beach, both of Calif.

[73] Assignee: U.S. Divers Company, Inc., Santa Ana, Calif.

[21] Appl. No.: 24,667

[22] Filed: Mar. 1, 1993

Related U.S. Application Data

[63] Continuation of Ser. No. 649,909, Feb. 4, 1991, abandoned.

[51] Int. Cl.[5] .......... A61M 16/00
[52] U.S. Cl. .......... 128/204.26; 128/205.24
[58] Field of Search .......... 128/201.27, 201.28, 128/204.26, 205.24

[56] References Cited

U.S. PATENT DOCUMENTS

| | | | |
|---|---|---|---|
| 3,467,137 | 9/1969 | Brown | 137/494 |
| 3,633,611 | 1/1972 | MacNiel | 137/494 |
| 4,140,113 | 2/1979 | Pedersen | 128/204.25 |
| 4,214,580 | 7/1980 | Pedersen | 128/204.26 |
| 4,446,859 | 5/1984 | Pedersen | 128/204.26 |
| 4,683,881 | 8/1987 | Hansen et al. | 128/204.26 |

FOREIGN PATENT DOCUMENTS 1925185 8/1970 Fed. Rep. of Germany .

*Primary Examiner*—Edgar S. Burr
*Assistant Examiner*—Aaron J. Lewis
*Attorney, Agent, or Firm*—George F. Bethel; Patience K. Bethel

[57] ABSTRACT

A second stage demand regulator is disclosed which has a regulator body with a spring loaded poppet valve mounted therein. A diaphragm mounted in said regulator body responds to pressure differentials to provide demand breathing gas to a user in communication with the regulator. The demand valving function is provided by the spring loaded poppet having a lever in contact with the poppet and the diaphragm. Upon acutation of the diaphragm, a greater mechanical advantage is initially provided to the lever through a point of contact with an operating surface that is closer to the axis of rotation than a second point of contact.

17 Claims, 5 Drawing Sheets

Fig. 3
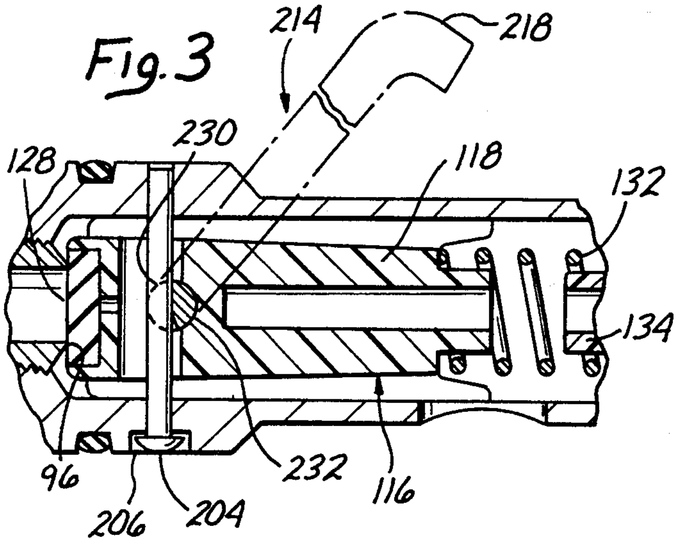
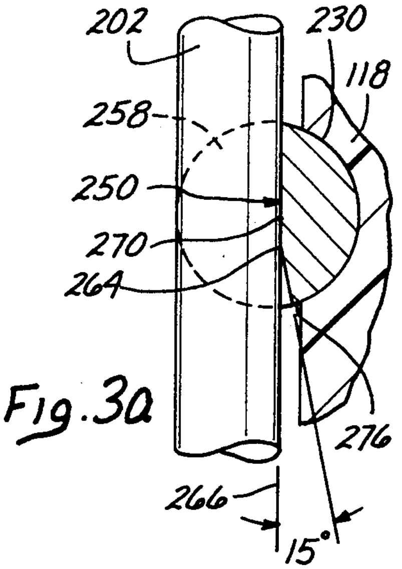
Fig. 3a
Fig. 4
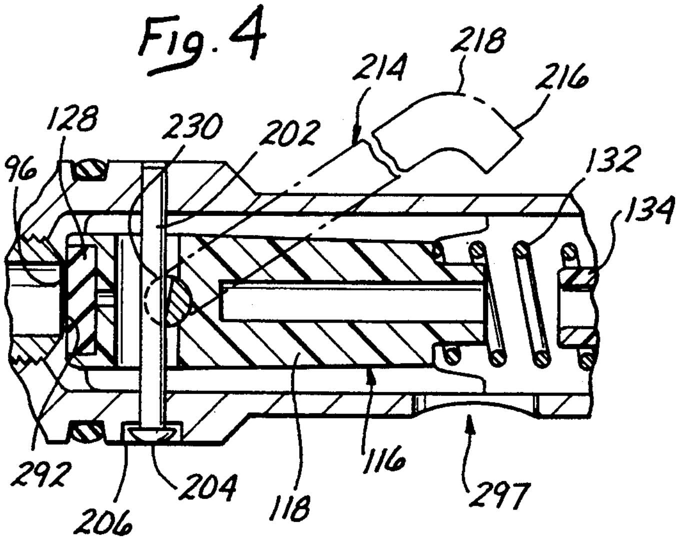
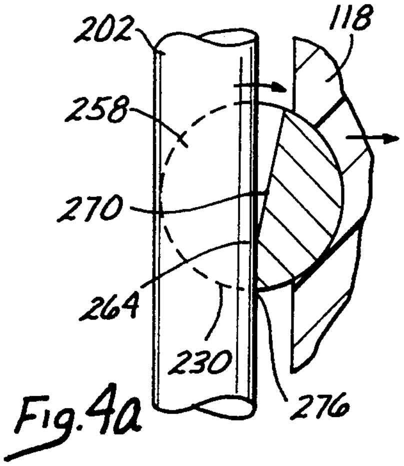
Fig. 4a
Fig. 5
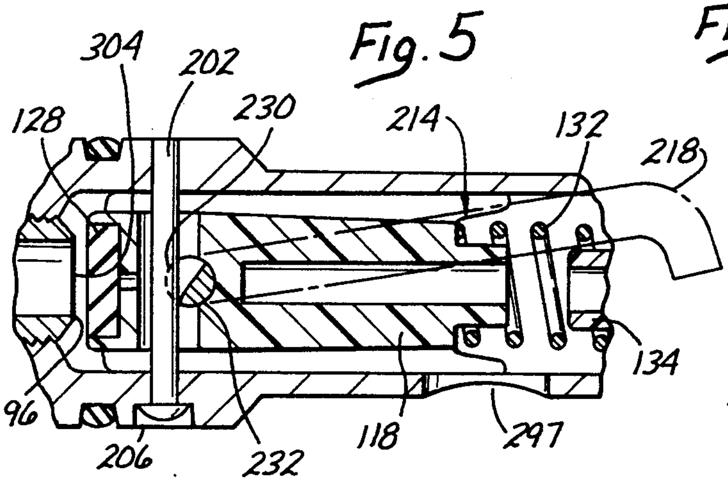
Fig. 5a
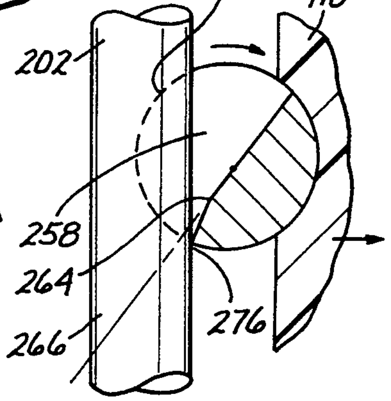

SECOND STAGE DEMAND BREATHING REGULATOR

This application is a continuation of application Ser. No. 07/649,909, filed Feb. 4, 1991, now abandoned.

FIELD OF THE INVENTION

The field of this invention lies within the field of self-contained breathing apparatus. More specifically, it lies within the field of breathing apparatus as it pertains to demand regulators. Such demand regulators are also known as second stage regulators. In many cases, they receive breathing gas from a first stage regulator that regulates gas from a high pressure source, such as a pressurized source of breathing gas in a tank. Regulation is by a demand function oftentimes provided by a diaphragmatic action that responds to a breather's inhalation. Such second stage demand regulators are used by industrial workers, firemen, and divers using self-contained breathing apparatus.

BACKGROUND OF THE INVENTION

The background of this invention resides within self-contained breathing apparatus which use a second stage or demand regulator. Such demand regulators have been known to utilize a diaphragm. The diaphragm is balanced between ambient pressure and pressure within the regulator. When pressure within the regulator is diminished by a diver's inhalation, the diaphragm moves and the regulator proceeds to function.

Movement of the regulator diaphragm generally causes a contacting lever, toggle, or other movable actuating member to move in response to the diaphragm. When such movement takes place, the movable member in contact with the diaphragm is moved in a manner to cause a valve or other sealing member to unseat. When the valve or other member unseats, it causes a flow of breathing gas such as compressed air from a source of high pressure regulated gas. Such high pressure regulated gas can be provided from a tank and first stage regulator.

Such demand or second stage regulators are known in the art for both divers and self-contained breathing apparatus for use with industrial and fire safety equipment. Most of them have an indigenous problem of rapid flow upon the valve opening. Fundamentally what happens is after the valve or means for valving the intermediate pressure initially takes place, the air or breathing gas then flows through the valve seat area more readily than it initially flows.

First of all, flow across the valve seat increases merely by opening and pressure pushing it after it has been unseated. Secondly, the air or breathing gas once it passes initially through the valve, creates a venturi effect within the regulator housing which causes a pressure drop and helps to draw down the diaphragm that contacts the lever which further opens the valve. This is in effect a valve opening enhancement function from the standpoint of overcoming spring pressure on the valve.

The valve is initially caused to move by the mechanical action, and is caused to move further by a second mechanical action. An idealization is to allow a greater mechanical advantage initially in the movement until the venturi or imbalance takes over and then provide a lesser mechanical advantage thereafter to move the valve.

The inhalation effort required to move the valve firstly is greater than the inhalation effort required to move it the remaining portion of movement. This is due to the fact that after initially opening, the venturi acting on the diaphragm and the imbalance across the valve draws it into a further opened position with greater ease. Generally, the internal design of the regulator should cause a near balance between the valve spring that closes the valve and the venturi effect and flow imbalance across the valve so that the regulator requires a minimal inhalation effort to sustain any particular flow that the user requires. Consequently, with regard to diaphragmatically operated second stage regulators, it would be preferable to have a greater mechanical advantage at the beginning of the movement and then subsequently a lesser mechanical advantage.

Such action creates an easier breathing regulator, inasmuch as less suction or inhalation is required due to greater mechanical advantage. After the initial opening, the lesser mechanical advantage allows for a smoother operation without a rush of air to the diver.

This invention solves the problem of the initial mechanical advantage being required in a greater magnitude through its unique lever system. The lever's contact of the poppet assembly, to cause it to move and open the valve, is incorporated within an enhanced angular orientation for greater mechanical advantage during initial movement. The poppet assembly is then moved with less mechanical advantage after initial opening when the air starts to pass through the valve and creates a venturi within the regulator housing acting on the diaphragm to push down the lever which increases the valve opening. This is caused by the lever at its opposite end from the diaphragm being provided with a first angle or contact point of engagement which is closer to the axis of rotation of the lever at its contact point for movement of the poppet assembly. The subsequent movement allows the placement of the contact point to be removed to a farther position from the axis of rotation. This creates a longer point of contact from the center of the radius of movement thereby causing greater effort, inasmuch as the mechanical advantage is reduced by the increased distance from the radius of movement.

Another drawback of the prior art is that the relative size of second stage regulators is generally large due to overall exhaust valve configurations. This invention overcomes the exhaust valve placement problem by creating two purge valves in an optimum position.

In particular, exhaust or purge valves in the past have been displaced from the main body of the second stage regulator to a significant degree. This is due to the fact that they were in the form of one large exhaust valve or in the alternative, two smaller valves which had to be placed in a removed location from the center of the regulator body.

This invention overcomes this deficiency by allowing angular placement for minimum cubic displacement. The angular placement places the exhaust valves in close proximity to the regulator valve body to provide for minimally sized orientation of the respective valves and regulator cubic displacement in which they are seated.

Another disadvantage of the prior art is that the delivery of breathing gas from the valve body oftentimes took place in an offset location. This invention allows for a delivery of breathing gas in a centrally oriented outlet with respect to the user's mouthpiece. When taken in consideration of the enhanced operation, this is an improvement in combination with the other portions of this invention.

Finally, an inventice consideration with respect to the structure of this second stage regulator appertains to the utilization of an easily removable cover for the exhaust valves. In the past, covers have not been readily removed from the exhaust valves for checking of such exhaust and purge valves. This invention allows a snap-on or tab and groove securement relationship for the cover. The tab and groove relationship is enhanced by the spring characteristics of the cover. It can be snapped into grooves and removed on a ready basis without the requirement of special tools and/or disassembling of the entire regulator to access the exhaust or purge valves.

Consequently, it is believed that this invention has numerous inventive characteristics attendant therewith both in their singular orientation and when taken in combination with each other.

SUMMARY OF THE INVENTION

In summation, this invention comprises a second stage or demand regulator with improved operating action provided by greater mechanical advantage in the initial movement of the valve with lesser mechanical advantage being required thereafter. Additionally, it provides for an improved geometrical configuration for optimum sizing and exhaust or purge valve placement and further incorporates an improved snap-on cover over the purge valves.

The invention incorporates a second stage regulator or demand regulator of extremely compact size. The compact size is in part created by the improved lever arm and purge valve arrangement. The improved lever arm is such where it can be shorter and more compactly placed than prior art second stage regulators.

The purge valves or exhaust valves are oriented two in number at an angle for enhanced sizing while at the same time creating a geometrical placement for the regulator body without extending the volume of the regulator body. This provides an improved placement for function, as well as a small size to the entire regulator.

Of significant importance is the operation of the lever in contact with the diaphragm and the poppet assembly. Operation is such wherein a greater mechanical advantage takes place initially for movement of the poppet assembly. Thereafter a lesser mechanical advantage takes over when further movement is experienced. This allows for the venturi effect resulting in diaphragm pull-down to enhance the movement and thereby requires less mechanical advantage of the lever so that a smooth operation of the valving function takes place.

The increased initial mechanical advantage is created by the lever engaging a surface such as a pin or other member at a point of contact removed from the axis of rotation of the lever. Further movement of the lever and point of contact is such wherein the contact point is removed to an extended position which provides lesser mechanical advantage. Nevertheless with the enhanced venturi effect on the diaphragm, it moves the valve to an open position with a smooth and relatively uniform action.

Finally, the cover for the purge valves or exhaust valves provides ready access. This ready access is through a snap-on cover which has tabs in association with grooves in the regulator body to allow for spring engaged retention of the cover.

Summarily stated, the invention provides for enhanced breathing functions, improved access, and lightweight with a compact configuration.

BRIEF DESCRIPTION OF THE DRAWINGS

The invention will be more clearly understood by reference to the description below taken in conjunction with the accompanying drawings wherein:

FIG. 3 shows a detailed sectional view of the lever and valve assembly shown in FIG. 1 with the lever starting its action with greater mechanical advantage to remove the valve seat.

FIG. 3a shows a greater detail of the interaction of the lever against the surface against which it operates.

FIG. 4 shows a detailed sectional view of the lever with the valve opening slightly and providing for flow through the greater mechanical advantage of the placement of the lever against its operating surface.

FIG. 4a shows a detailed view of the operating surfaces of the lever.

FIG. 5 shows a sectional view of the lever with its lesser mechanical advantage mode operating against the operational surface.

FIG. 5a shows a greater detail of the contact point of the lever against the operational surface.

DESCRIPTION OF THE PREFERRED EMBODIMENTS

Figure 1:
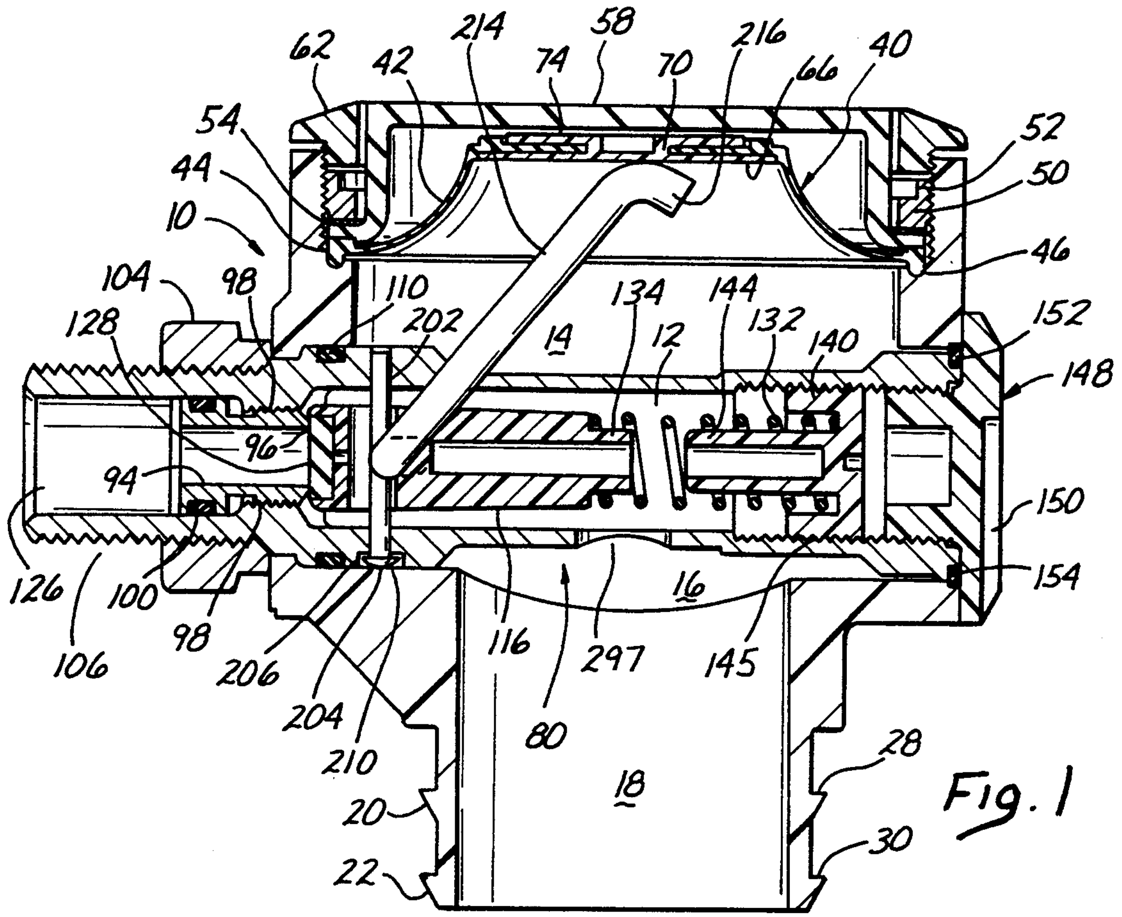
FIG. 1 shows a sectional view of the regulator of this invention along a midline thereof.
Figures 2, 6:
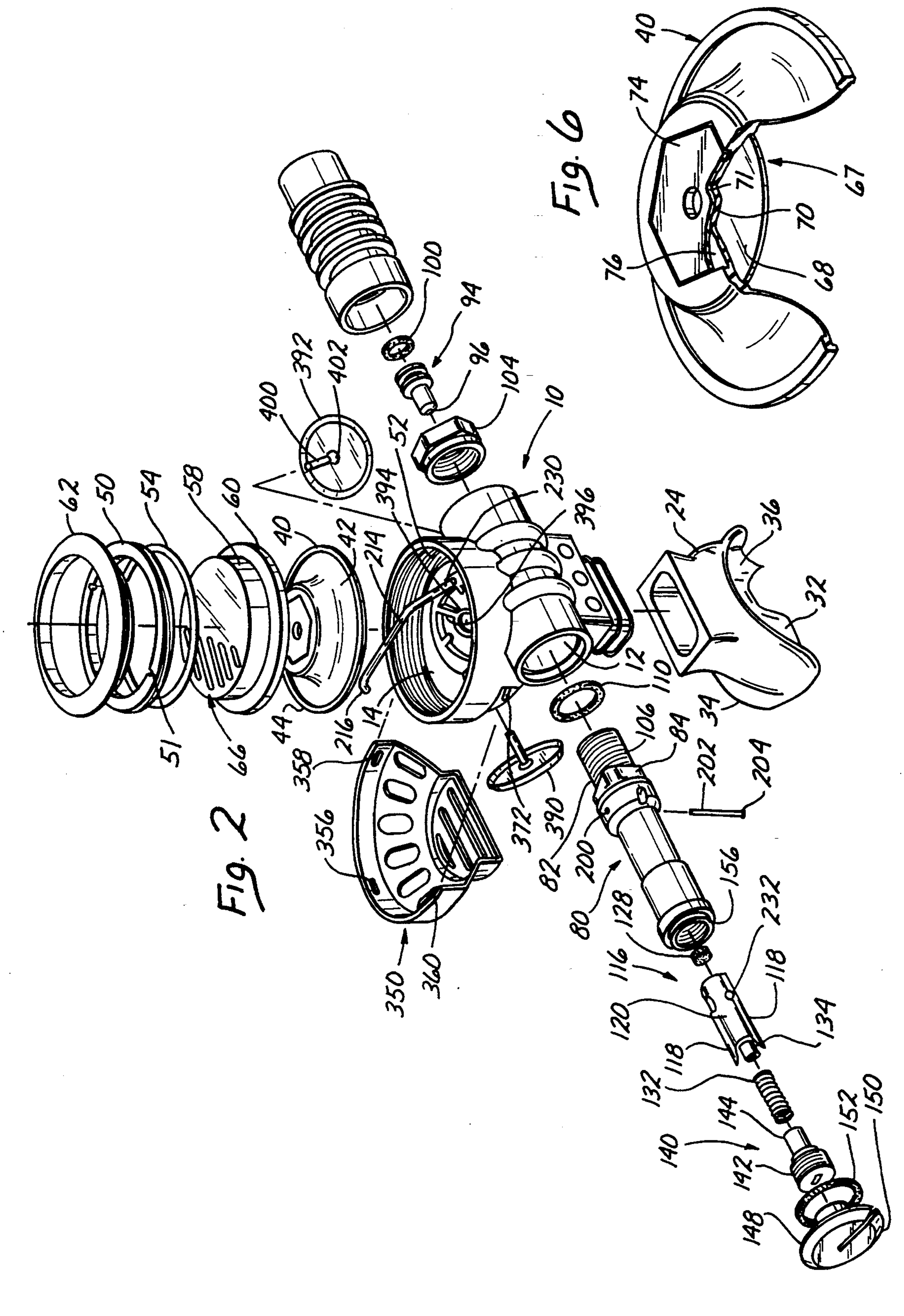
FIG. 2 shows a perspective exploded view of the regulator.
FIG. 6 shows a perspective partially sectioned view that has been fragmented in part of the diaphragm and its contact plate for the lever.

Looking at FIG. 1 in conjunction with FIG. 2 it can be seen that a housing for the second stage regulator or demand regulator of this invention has been shown. In particular, a housing 10 has been shown of a unitary casting which can be plastic or metal. The unitary cast configuration incorporates a round cylindrical chamber 12 which receives the valve functions as will be detailed hereinafter. The cylindrical chamber 12 is provided in the regulator body 10 in a longitudinal direction and commensurate with a cavity 14. The cavity 14 receives the operative elements as will be detailed hereinafter.

Connected to the cylindrical chamber 12 and the upper cavity 14 is an outlet chamber 16. The outlet chamber 16 continues into a rectangularly cross sectioned outlet 18. The outlet 18 is formed by rectangular walls having flanges or tangs 20 and 22. The tangs or flanges 20 or 22 receive a mouthpiece 24 as can be seen in FIG. 2. The mouthpiece 24 is received over the barbs or tangs 20 and 22 in order to secure the mouthpiece in place.

Generally, the mouthpiece is formed of an elastomeric silicon rubber or plasticized material which is suitably formed so as to be able to expand over the tangs or barbs 20 and 22 which form the flanges. The mouthpiece 24 does not tend to back off inasmuch as the tangs, flanges or barbs 20 and 22 have an inclined surface to receive the mouthpiece thereover, but impede the withdrawal somewhat over the flattened surfaces 28 and 30 of the flanges 20 and 22. This is because of the fact that interior flanges of the mouthpiece 24 tend to lock on and form an elastomeric grip around the mouthpiece outlet 18.

Any type of mouthpiece can be utilized. However, it has been found that the most effective mouthpiece provides for sufficient bite and comfort by means of lip flanges 32 and 34. The lip flanges are received in the lips and a bite can be taken on a bit portion 36.

Looking more particularly at the upper chamber 14, it can be seen that a diaphragm 40 has been shown. The diaphragm 40 is formed of an elastomeric bell-shaped member so that it can flex inwardly into the cavity 14. The elastomeric bell-shaped member 40 is formed with a curved surface 42 which slopes downwardly to an expanded circular flange 44. The expanded circular flange 44 is received in the regulator body 10 by virtue of a groove 46 receiving a circular protuberance of the flange 44 therein. The diaphragm is held in place by means of a retainer ring 50 which threads downwardly into threads 52 provided in the body 10. The retainer ring 50 threads against a washer 54 which is in turn seated against a cover 58. The cover 58 has an expanded base 60 against which the washer 54 is seated and which the retainer ring 50 is threaded against. By threading downwardly on the retainer ring, the entire assembly including the cover 58, retainer ring 50 and washer 54 are seated in tight juxtaposition against the diaphragm flange 44 to secure it in place.

In order to provide for a pleasing and aesthetic appearance, a decorative ring 62 is threaded downwardly on top of the retainer ring 50 to provide for a color matching to the regulator. The ring 62 also allows for a covering and protection of the retainer ring 50 so that it will not be disturbed. It provides a cover for the retainer ring 50 and in particular prevents dislodgment by movement of an object against the threading tool insets 51 of the retainer ring 50.

In order to permit ambient pressure and orientation of fluidic balance of the regulator diaphragm 40, a number of ports 66 are provided within the cover 58. These ports 66 can be of any configuration. In this particular case they have been shown as elongated ports diminishing to a lesser port of elongation on one side of the face of the cover 58.

Looking more specifically at the diaphragm 40 as can be seen in FIGS. 1, 2 and 6, it can be seen that a spool 67 has been connected to the diaphragm. The spool 67 is such where it has a rounded spool-like configuration on the inside. In particular, an interior spool disk portion which has been rounded in the form of rounded spool 68 is shown with a necked-down portion 70. The necked-down portion 70 passes through an opening of the diaphragm 40.

The necked-down protion 70 is of a hexagonal shape and sits in a snug configuration within a hexagonal opening 71 of the diaphragm 40. The hexagonal opening receives the hexagonal portion 70 as it passes therethrough. After the hexagonal portion 70 passes through the diaphragm, it expands into an enlarged hexagonal portion 74. The enlarged hexagonal portion 74 is seated within a hexagonal opening or indentation 76 on the outer surface of the diaphragm. The inner portion of the spool 68 is placed interiorly within the diaphragm 40 in a relatively snug position. The hexagonal interconnecting spool portion 70 passes through the matching hexagonal opening 71 of the diaphragm to an expanded hexagonal portion 74 seated within the hexagonal opening or indentation 76 on the exterior of the diaphragm 40. The entire assembly can be put together by stretching the hexagonal opening 71 of the diaphragm 40 which receives the hexagonal minor portion 70 and allowing the diaphragm to stretch into the space between the interior rounded disk of the spool 68 and the exterior hexagonal portion 74. The hexagonal portions of the diaphragm 40 can be substituted by flat-sided members such as triangular, square, and pentagonal members, or other forms which will limit turning of the disk 68.

A valve body 80 is shown in the figures and can be seen as being received within the cylindrical opening 12. The valve body 80 comprises a major portion of the operative assembly and receives the operative components of the valve. The valve body 80 can be generally formed from a single cylindrical member that has been machined to fit into the cylindrical opening 12. In order to have a proper fit and orientation, flats 82 and 84 can be seen. These flats 82 and 84 serve to match the interior cylindrical opening surfaces so as to properly orient the body 80 in the position to allow for flow. One flat is larger than the other and is received within an interior like flat of the cylindrical opening 12 so as to orient the body 80 correctly.

The valve body 80 is inserted and seated by means of threaded members received on either end which secure the body into the interior 12. It can be slid from the left side of FIG. 2 looking at the drawing.

An orifice or valve seat 94 in the form of a cylindrical member is threaded into the valve body 80. The orifice 94 has a chamfered valve edge 96 which allows the valve seat to be seated thereagainst. This edge 96 has sometimes been referred to as a valve seat, however for purposes of consistency, the cover thereover as described herein will be referred to as the valve seat. The orifice seat or valve seat can be threaded into place within threads 98 of the valve body 80. It is sealed with respect to pressure flow by means of an O ring 100. The O ring 100 seats the orifice seat with the chamfered edges 96 in a position to prevent gas passage around the orifice seat.

In order to connect the valve body 80 into tightened juxtaposition into the cylindrical opening 12, a hex nut 104 is provided. The hex nut 104 threads down onto threads 106 of the valve body 80, thereby securing it after the valve body passes through the cylindrical opening 12.

In order to seal the valve body 80 into the interior of the body 10 of the regulator, an O ring 110 is utilized. This O ring 110 is such wherein it seals the exterior surfaces of the valve body 80 as it sits within the cylindrical opening 12 of the regulator body 10.

The valving function and movement of the valve seat from off of the edges 96 of the orifice seat is provided by movement of a poppet assembly 116. The poppet assembly 116 comprises an elongated cylindrical member which has ridges 118 extending axially along the four quadrants. The four axial quadrant ridges 118 allow for the poppet assembly to slide backwardly and forwardly and at the same time allow for passage of gas along axial spaces 120 between the ridges 118. Smooth sliding movement back and forth within the valve body interior assembly 80 is provided along the axial ridges 118 while at the same time allowing fluid to flow within the elongated spaces 120 therebetween.

To provide for a valving function of the gas as seen at the intermediate pressure end of the inlet side of the regulator, namely inlet 126, a valve seat or poppet cover 128 is utilized. The valve seat or cover 128 is placed within a depression or an insert of the poppet assembly 116. The seat 128 once seated will generally not move form its orientation it is placed in so that it will continue to valve against the orifice seat or chamfered surface 96.

The poppet assembly 116 is driven by means of a spring 132 formed as a compression coiled spring. The interior of the compression coiled spring 132 seats over a rounded cylindrical portion 134 of the poppet assembly so that it can be driven thereagainst and cause the seat or cover 128 to be implaced against the surface 96 for closing off gas flow.

At the other end of the spring 132, a threaded member in the form of an adjusting screw 140 is provided. The adjusting screw 140 has threads 142 and a cylindrical portion 144 which receives the interior of the coil spring 132. When seated thereover, the compression of the spring 132 can be adjusted by rotating the adjustment screw 142 inwardly and outwardly in the threads 145 of the valve body 80 to create greater or lesser spring pressure.

In order to cap off and seal the valve body 80 and the adjusting screw 140, a cap nut 148 is utilized. The cap nut 148 also threads into the threads 145 by means of a slot 150 of the cap nut. the cap nut 148 is sealed by means of an O ring 152. The O ring 152 is held in place by an overturned surface or outwardly circumferential flange 154 of the valve body 80. In effect, a slight upturned flange 154 is provided which allows the O ring 152 to be seated in the groove thereunder and not be removed over the edge without removing it over the upturned edge 154 of the valve body 80.

A diametric bore 200 is shown passing through the valve body. This diametric bore 200 receives a pin 202 passing therethrough. The pin 202 has a head 204 seated within a countersink 206. The pin 202 moves freely within the bore 200 across the axis of the valve body 80. Thus, it normally rests against the inside surface 210 of the regulator body 10 and can be displaced upwardly into the space of the countersink 206 overlying the pin head 204 as seen in FIG. 1 within the bore 200.

A key element of this invention is a lever 214. The lever 214 has an upper portion 216 which is turned over providing a rounded surface 218 which is engaged against the interior of the disk or spool 67 rounded spool portion 68. This rounded surface 218 seated against the interior disk portion 68 allows it to ride thereagainst so that when the diaphragm 40 is displaced into the chamber 14, it moves the lever 214 into the chamber.

The lever 214 terminates with a cross member, lateral arm, or cross extension 230. The cross member or lateral arm 230 is placed within an opening 232 of the poppet assembly 116. The implacement within the opening 232 of the poppet assembly 116 allows the lateral arm 230 to move about its axis freely therein as only restricted by a machined surface 250 which can be seen in FIGS. 3, 4, 5 and 3*a*, 4*a* and 5*a* more clearly. The mechanical surface 50 seats against the pin 202, which forms the fixed operating surface against which the lateral arm can operate.

This surface 250 is machined so as to form a groove 258 across the diameter of the cross member or lateral arm 230 of the lever 214. The surface 250 of groove 258 is normally implaced against the pin 202 by virtue of the loading of spring 132 forcing the poppet assembly 116 into the leftward position as shown in FIGS. 3, 4, 5, 3*a*, 4*a*, and 5*a*. When the flat of the lateral arm formed by diametrically machined groove surface 250 that can be seen in groove 258 is allowed to engage the pin 202, it provides for a seating against the pin and an operating surface against the pin 202.

In the position shown in FIGS. 3, 3*a* and 1 with the lever 214 in the upwardly cocked position, the flat 250 of the groove 258 rests against the outside surface of the pin 202.

As the diaphragm 40 is pulled inwardly by inhalation, the machined surface point of contact becomes point 264. The point 264 is formed by a 15° machining from the diametric line 266 in a position removed from the axis 270 of the cross bar 230 of the lever. The distance between the axis 270 and the contact point 264 is dependent upon the amount of mechanical advantage which is desired and a desire to obtain sufficient contact at point 264 against the pin 202. The closer point 264 is to the axis 270, the greater the mechanical advantage.

The diaphragmatic movement inwardly causes the lever 214 to move downwardly as shown in FIGS. 3 through 5 and FIG. 1. The mechanical advantage is greatest through the movement of the cross member or lateral arm 230 at point 264 until contact at point 276 is realized, as shown in FIGS. 4 and 4*a*. When contact of point 276 is realized, the mechanical advantage is lessened significantly. This is where it starts as shown in FIGS. 4 and 4*a*. At this point, the lever 214 has moved through an arc of approximately 15° and the lateral arm 230 through a radial arc of 15°, which is tantamount to the machined surface having the 15° machining from point 264 through point 276.

Looking more particularly at FIG. 5, it can be seen that the end point 276 has been engaged beyond is initial contact seen in FIGS. 4 and 4*a* for further movement against the pin 202. At this point, the full radius of the cross section of the member 230 is realized, thereby creating less mechanical advantage.

The initial increased mechanical advantage of movement as seen in FIGS. 3 through 4 and 3*a* and 4*a* across point 264 enables the valve as seen in FIG. 4 to be removed to provide a nominal space 292 through which the passage of gas can take place across the valve seat or cover 128 and orifice edges 96. At this point, gas moves along the slots or passages 120 between the fins or uprights 118. The gas then moves through the valve body 80 outwardly through an opening 297. The passage through opening 297 downwardly into the larger chambers 16 and 18 creates a venturi effect so that less mechanical advantage is required to move the valve further. This is due in great measure to the diaphragm being pulled down or inwardly by the venturi effect. This lesser mechanical advantage is incorporated within the movement from point 276 through the rest of the opening movement. This movement of the lever 214 and attendant lateral arm 230 provides a further opening between the valve seat 128 and the surface 96 as can be seen in FIG. 5, namely opening 304. At this point, a full breath has generally been taken and the spring 132 returns the valve seat 128 to its covering position over the surface 96.

Summarily stated, as seen in FIGS. 3 through 5 and the detailed FIGS. 3*a*, 4*a* and 5*a* thereof, a greater mechanical advantage is used upon the initial inhalation or deflection of the diaphragm 40 by virtue of the movement of the point 264 against the pin 202. As the cross member 230 moves such that point 276 of the 15° surface contacts pin 202, the mechanical advantage is then diminished as further rotation on point 276 takes place. This provides for increased mechanical advantage when necessary to unseat the value and a lesser mechanical advantage after the flow of air through opening 292 has taken place.

The lateral arm 230 can be provided with any cross section such as a rectangle, triangle, arcuate member, or combination. The requirement is that a point of contact of the arm 230 against an operating surface, such as pin 202 must first be at a point providing greater mechanical advantage, which is generally closer to the axis of rotation of the arm, from that of a second contact point more distal than the first from the axis of rotation.

Figure 8:
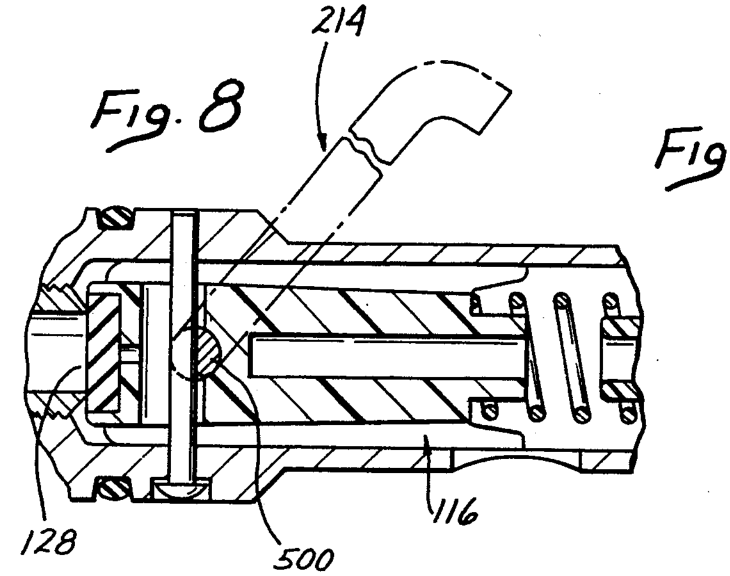
FIG. 8 shows a sectional view of the poppet assembly and lever initially contacting the surface for greater mechanical advantage.
Figure 8A:
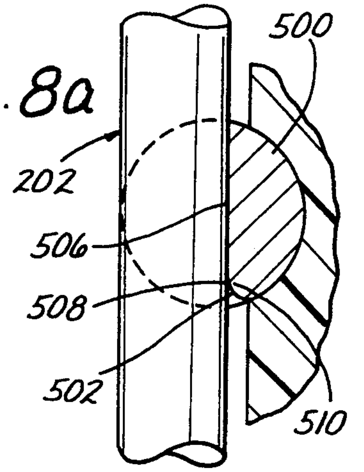
FIG. 8a is a detailed showing of the contact surface of the lever shown in FIG. 8.
Figure 9:
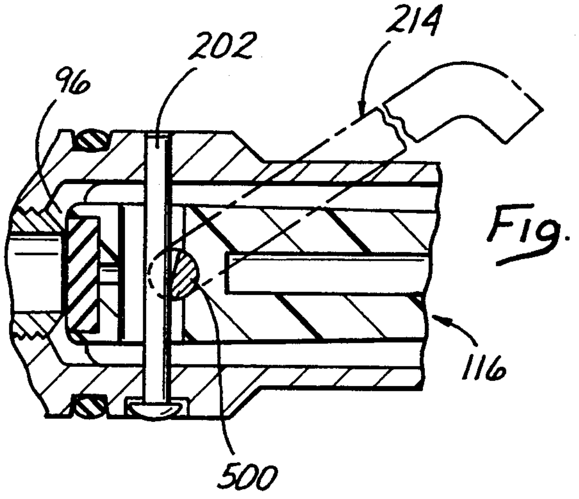
FIG. 9 is a cross sectional view of the lever and contacting surface as it moves from a greater mechanical advantage to a lesser mechanical advantage.
Figure 9A:
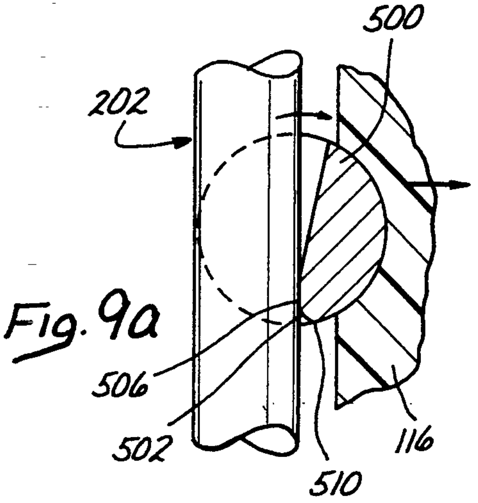
FIG. 9a is a detailed view showing the contacting surfaces as shown in FIG. 9.
Figure 10:
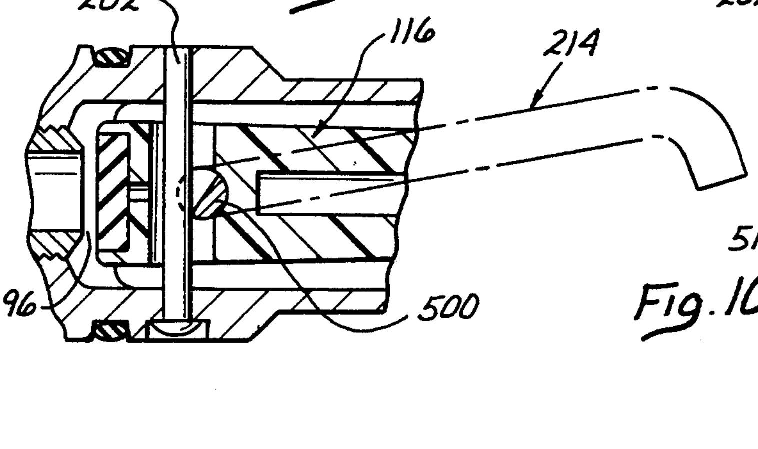
FIG. 10 is a cross sectional view showing the lever in a lesser mechanical advantage mode.

FIGS. 8, 9 and 10 respectively characterize the lateral arm 230 in a different configuration with different operating surfaces. In particular, looking at the lateral arm of the lever 214, it can be seen that a different lateral arm configuration 500 has been shown in the form of a rounded cam surface 502. The rounded cam surface 502 is machined into the arm 500, as shown, or in the alternative it can be formed entirely of a member having the configuration shown in FIGS. 8 through 10.

Figure 10A:
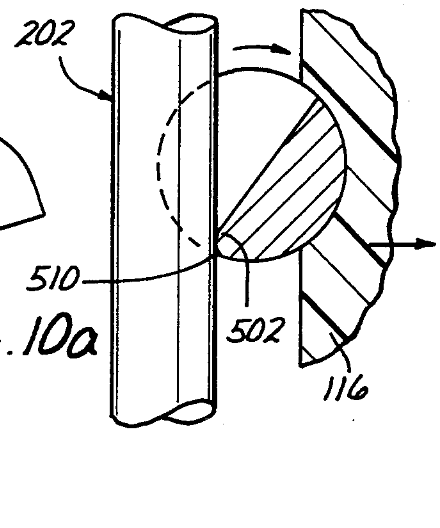
FIG. 10a is a detail of the showing in FIG. 10.

In particular, the lateral arm 500 can be machined or formed entirely with the cross section from the turning point of the lever 214 to the end or it can be machined only in the part where it engages the pin 202. The lateral arm 500 operating surface has been shown with the curved cam surface 502 which continues in a rounded manner from a flat 506 at a particular point or ending of the flat 508 to the terminal point 510. This point 506 initially provides greater mechanical advantage as the lateral arm 500 turns about its axis of rotation. This greater mechanical advantage starting at 506 can be such where the curve of the surface 502 becomes eccentrically greater when extending towards the point 510 so that a lesser mechanical advantage is experienced along the entire surface of the curved portion 502. In effect, the curved surface 502 can be provided as a cam so that the mechanical advantage decreases progressively along the contact point of the curved surface, rather than waiting until the contact point at the end, namely point 510, is reached as shown in FIG. 10*a*. Thus, the curved or cammed surface 502 can decrease the mechanical advantage as the lateral arm 500 turns about its axis of rotation such that the mechanical advantage steadily decreases until point 510 is contacted. At such time the mechanical advantage as decreased, will maintain the same as the lateral arm 500 continues its movement beyond point 510.

Other cam surfaces and embodiments can be utilized wherein the operating surface of the lateral arms 230 or 500 can be of any suitable configuration. The one consideration is that the initial mechanical advantage should be greater and thereafter it should decrease. As to whether it should be decreased in a continuum as shown in FIGS. 8 through 10 depends upon the operating characteristics of the poppet assembly 116 and the overall flow characteristics enhanced by the venturi after opening of the valve as shown in FIG. 9.

Figure 11:
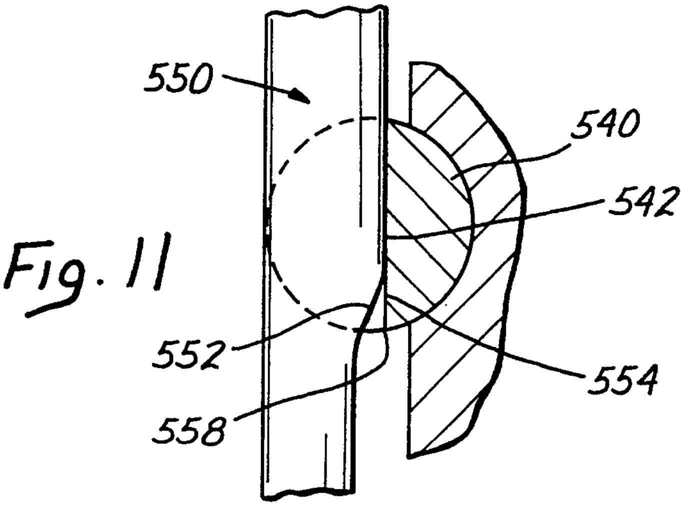
FIG. 11 shows a detailed sectional view of the lever with a flattened surface in an operative mode against a cammed surface.
Figure 12:
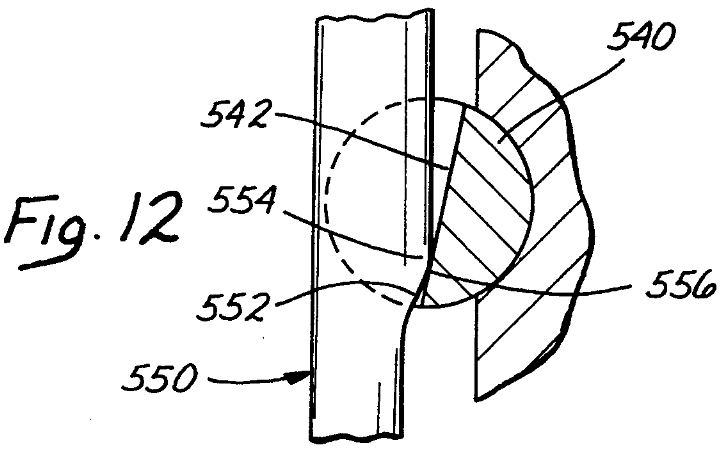
FIG. 12 shows the lever of FIG. 11 in a mode where it is beginning to provide less mechanical advantage on a cammed operating surface.
Figure 13:
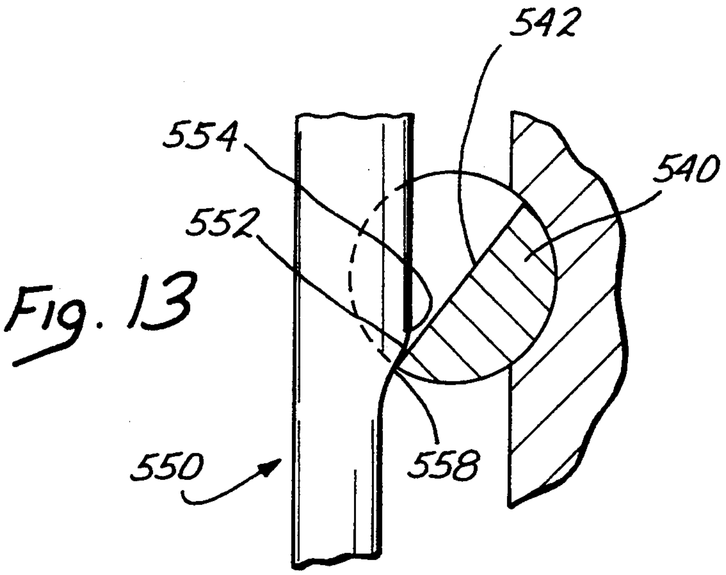
FIG. 13 shows the lever of FIG. 11 in a mode finishing its operation through the lesser mechanically advantaged operating surface.

Looking more particularly at FIGS. 11 through 13, the lateral lever arm analogous to lateral arm 230 and 500 is shown as lateral arm 540. Lateral arm 540 can be machined into the lever 214 as previously described or it can be a continuous flat from the turn of the lever 214. In this embodiment, the continuous flat is shown as a diametrical flat surface 542. However, this diametrical flat surface can be provided in whole or in part and moved with respect to the axis of the lateral arm 540, so that it does not have to cut across the diameter, but can be formed as a segment or chord less than the diameter.

In FIGS. 11 through 13, the pin 202 has been substituted by a portion seated with respect to the poppet 116 in a manner that it can engage the lateral arm 540. In this case, the surface can be a bar, a machined element, or any other portion of the regulator, so long as the poppet 116 can move backwardly and forwardly with respect thereto.

The member against which the lateral arm 540 operates, is member 550. Member 550 has a cam or curved surface 552. The cam surface 552 is curved in a manner so that the flat 542 engages it in a rolling manner so that the initial point of contact 554 provides a greater initial mechanical advantage until it moves to the contact point 556 of FIG. 13. After moving over the cam surface 552 to the fullest extent, contact point 558 engages the curved surface 552 to provide lesser mechanical advantage. The surface 552 can be of any suitable configuration, so long as it allows engagement of the flat 542 against the curve 552 for increased mechanical advantage at the initial contact point 554 and decreased mechanical advantage at 558. In like manner as the previous embodiment in FIGS. 8 through 10, the operating surface 552 against which the lateral arm 540 operates can be curved so as to provide a cam movement for continuing decreased mechanical advantage as it moves from point 554 to the last point of contact 558.

With regard to the foregoing configurations of FIGS. 8 through 13, the essence is that an increased mechanical advantage is experienced through either the curve or surface of the lateral arm analogous to lateral arm 230 or by a cammed curve of an operating surface 550 analogous to pin 202. The mechanical advantage from an increased to a decreased point can be a stepped difference, or in the alternative, a continuing decreased mechanical advantage. One skilled in the art can provide various reacting surfaces of the lateral arm or the surfaces against which it reacts, causing the mechanical advantage to vary from a greater to a lesser mechanical advantage, either as a one step increment or a gradual cammed decrease of the mechanical advantage.

A further enhancement of the regulator can be seen by way of a cover 350 having openings therein which snap onto the outer surface of the regulator body 10. The cover 350 has tabs 358 and 360 that seat into openings on either side, one of which, namely opening 372 can be seen on the left of FIG. 2. An upstanding surface 374 can be seen in FIG. 7 which receives tab 356 seated thereover.

The cover 350 is made from a relatively flexible plastic so that engagement of the tabs 358 and 360 into respective openings 372 allows for a sprung placement and removal of the cover without special tools. This sprung removal and placement by the tab 356 seating against surface 374 and the tabs 358 and 360 respectively being seated in openings 372 on either side, allows for easy access to the purge valves that can be seen in FIGS. 7 and 2 wherein one has been removed. The valves 390 and 392 are formed as mushroom valves having a stem and a chamfered surface for sealing, as is known in the art. Specifically, purge or exhaust valves 390 and 392 are shown seated within small openings 394 that are centered in a triangular web provided by web members 396 that support the outer side of the exhaust valve. In order to pull the exhaust valves 390 and 392 into the openings 394, a stem 400 is utilized having a bell-shaped portion 402 at the base with an undercut which seats over the edge of the openings 394. This allows for elastomeric seating therein in the most optimum manner.

Through the angular orientation of the exhaust valves 390 and 392, a minimized volume or cubic displacement as to space is realized which enhances the overall size and characteristics of the regulator to create a diminished volume and at the same time superior performance.

Figure 7:
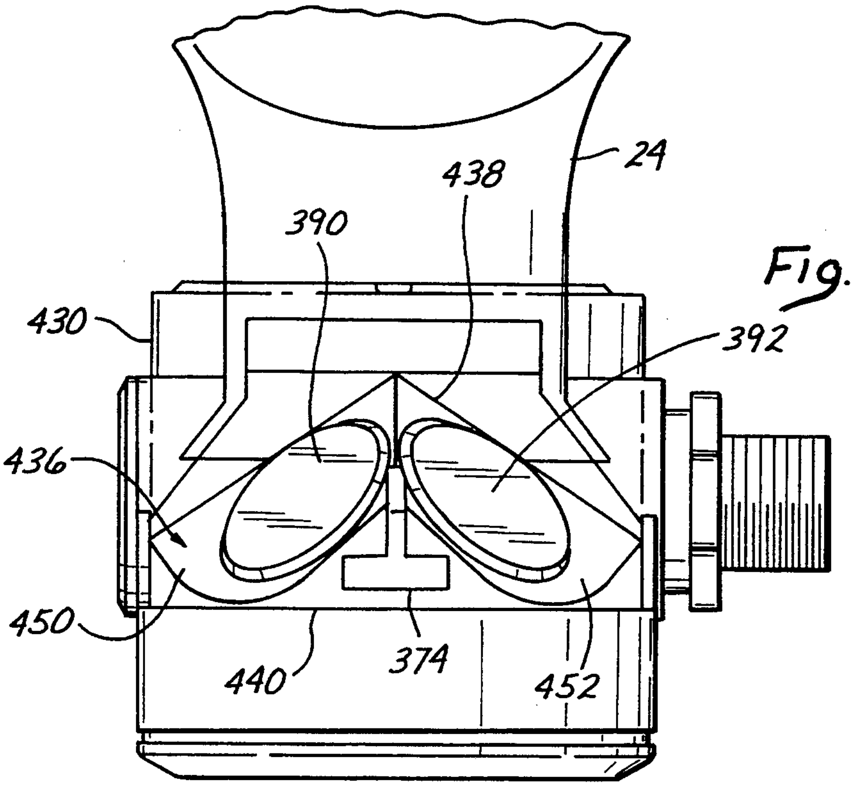
FIG. 7 shows a plan view of the purge valves or exhaust valves of the regulator looking upwardly in the direction of FIG. 2 with the cover removed.

Generally, a significant amount of exhaust or purge valving is required. This is usually accomplished by either a very large valve or two moderately sized exhaust valves, such as those shown as valves 390 and 392. In order to place them in a proper location for volumetric efficiency in the prior art, the interior chamber 14 was expanded into the dotted configuration 430 as shown in FIG. 7.

The enhanced configuration of this invention is established by an angled mounting wall 436. The angled wall is formed by two intersecting angled wall portions 450 and 452 for seating each valve 390 and 392 and forms a portion of the cavity 14.

This angled wall 436 as can be seen would normally fill out an area for seating of the purge valves in the rectangular or rounded configuration along the dotted line 430. However, with its angled surface at the base not only along the angular line 438, but also sloping backwardly in the direction of the line 440, it can be seen that a diminished space is required for seating and maintaining the exhaust valves 390 and 392. The two chamfered surfaces can be described as surfaces 450 and 452 which slant backwardly toward line 440 and forwardly in the direction of the base line 438. An enlarged area of wall surface provided by walls 450 and 452 is created while at the same time a diminished volume through a portion of a triangular volumetric surface is created. This triangular volumetric interior surface allows for the purge valves 390 and 392 to be properly seated while at the same time creating less volume and thereby less overall space or cubic displacement of cavity 14 and attendant volume and outer measurements of the entire regulator body 10. Thus, a definition of the angular walls backwardly, which respectively provide seating for the exhaust valves 390 and 392 is accomplished in a facile manner while at the same time creating an overall enhanced operative effect to the regulator.

The enhanced operation and general features of this invention should be read broadly in light of the following claims hereinafter set forth.

We claim:

1. A regulator for demand regulation of air or breathing gas comprising:

a regulator body;

a valve body mounted within said regulator body;

a diaphragm in said regulator body which responds to pressure differentials on either side of said diaphragm;

a breathing gas chamber in communication with said diaphragm and also in communication with at least one exhaust valve;

spring loaded poppet means within said valve body for valving gas into said regulator body; and, lever means in contact with said diaphragm having a lateral arm portion with an axis of rotation substantially parallel to the lateral arm portion for movement about its axis by said lever movement and in contact with said poppet means distally from said diaphragm, said lateral arm portion being in contact with a fixed operating surface the surface of said lever lateral arm portion contacting said fixed operating surface cooperatively forming an interface between them providing at least a first and second point of contact as it moves through its axis of rotation wherein said lever lateral arm portion provides a greater mechanical advantage of movement when contacting said fixed operating surface at said first point of contact in its initial movement by said diaphragm and a lesser mechanical advantage at said second point of contact after initial movement during inhalation.

2. The regulator as claimed in claim 1 wherein:

said poppet means comprise a valve seat; and, said valve body comprises a valve edge against which said valve seat can be seated.

3. The regulator as claimed in claim 2 wherein:

said lever's greater mechanical advantage is provided by said lateral arm rotating through its axis of rotation and having a surface with said first and second points of contact for engaging said fixed operating surface.

4. The regulator as claimed in claim 3 wherein:

said lateral arm of said lever is provided with a first contact point; and, a second contact point is provided further removed from the first contact point with respect to the axis of rotation of the lateral arm.

5. The regulator as claimed in claim 4 wherein:

said further contact point is at the outer surface of said lateral arm.

6. The regulator as claimed in claim 5 wherein:

said valve body has an opening centrally oriented to a breathing gas outlet.

7. The regulator as claimed in claim 6 wherein:

said diaphragm has a first rounded plate interiorly thereof for contacting said lever;

a second plate external therefrom having at least three sides thereto;

a connecting portion between said plates passing through said diaphragm having at least three sides therethrough; and, an indentation in said diaphragm for receiving the outer plate therein.

8. The regulator as claimed in claim 3 wherein:

said lateral arm has a groove across its axis; and, said groove engages said fixed operating surface of said valve body.

9. The regulator as claimed in claim 8 wherein:

said groove of said lateral portion of the lever arm is formed through the cross section of said lateral arm; and, a second surface is formed intersecting said first surface at a distance less than the radius of the first groove.

10. The regulator as claimed in claim 1 further comprising:

a cover overlying said exhaust valves having at least two tabs thereon;

grooves within said regulator body for receiving said tabs; and wherein, said cover is of sufficient resiliency to allow for spring loaded engagement of said tabs within the grooves of said regulator body.

11. The regulator as claimed in claim 1 wherein:

said exhaust valves are mounted in the regulator body within two respective walls which are angled to each other.

12. A demand regulator for regulating gas from a higher pressure to a pressure suitable for breathing comprising:

a regulator body having a valve body mounted therein;

a spring loaded poppet valve for valving gas from a higher pressure to a lower pressure;

a diaphragm which responds to a user's inhalation by moving into the regulator body; and, linkage means between said diaphragm and said poppet valve for movement of said poppet comprising a lever having a portion in contact with the diaphragm and a lateral arm having an axis of rotation substantially parallel to the lateral arm portion defining rotational movement of said lateral arm through its axis and in contact with said poppet valve said lateral arm further having a first contacting surface and a second contacting surface distally removed from the first contacting surface with respect to its axis of rotation.

13. A new and improved regulator for regulating a source of breathing gas from a higher pressure to a lower pressure for a user on a demand basis comprising:

a regulator body having a chamber in communication with an outlet to a breather and further providing at least one exhaust valve in communication with said chamber and outlet;

a diaphragm mounted in said regulator body having an interior portion exposed to said chamber;

a valve body mounted within said regulator body;

a spring loaded poppet mounted within said valve body having a valve seat thereon for sealing gases through said valve body at one end and a spring at the other end for causing said poppet to be seated in its normal position;

a lever with a lateral arm extending from said poppet from the lateral arm thereof into said chamber for contacting said diaphragm and having an axis of rotation substantially parallel to the lateral arm portion, said lateral arm oriented to said lever for movement about said lateral arm's axis of rotation when moved by said lever;

means for causing said lateral arm to engage said poppet at one portion thereof; and, at least two contact points on said lateral arm comprised of a first and second point wherein said second point is distal from said first point as to the axial orientation of said lateral arm and which engage a surface for movement of said poppet when the respective points contact said engagement surface.

14. The regulator as claimed in claim 13 wherein:

said poppet is adjusted as to pressure by an adjustment screw against which its spring seats, which threadedly engages said valve body.

15. The regulator body as claimed in claim 14 wherein:

the engagement surface for said lateral arm comprises a member extending across said lateral arm.

16. The regulator as claimed in claim 15 wherein:

said engagement surface comprises a pin.

17. The regulator as claimed in claim 13 wherein:

at least two contact points of said lateral member of said lever are formed by a groove within said lateral member having two intersecting surfaces wherein the intersection forms the first point of contact and a distal contact point is formed from said first point.

* * * * *